(12) United States Patent
Jeong et al.

(10) Patent No.: US 8,981,043 B2
(45) Date of Patent: *Mar. 17, 2015

(54) CATALYTIC SYSTEM FOR CO$_2$/EPOXIDE COPOLYMERIZATION

(75) Inventors: Jisu Jeong, Daejeon (KR); Sujith Sudevan, Daejeon (KR); Myungahn Ok, Daejeon (KR); Jieun Yoo, Daejeon (KR); BunYeoul Lee, Suwon-si (KR); SungJae Na, Suwon-si (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,723

(22) Filed: Sep. 12, 2012

(65) Prior Publication Data

US 2013/0131308 A1 May 23, 2013

Related U.S. Application Data

(62) Division of application No. 12/817,588, filed on Jun. 17, 2010.

(30) Foreign Application Priority Data

Jun. 18, 2009 (KR) .......................... 10-2009-0054600

(51) Int. Cl.
| | | |
|---|---|---|
| C08G 64/02 | (2006.01) | |
| C08G 65/26 | (2006.01) | |
| C07F 15/06 | (2006.01) | |
| C07C 39/23 | (2006.01) | |
| C07C 249/00 | (2006.01) | |

(52) U.S. Cl.
CPC ........ C08G 64/0208 (2013.01); C08G 65/2603 (2013.01); C08G 65/266 (2013.01); C07F 15/065 (2013.01)
USPC ............. 528/405; 528/395; 568/716; 556/32; 558/302

(58) Field of Classification Search
None
See application file for complete search history.

(56) References Cited

U.S. PATENT DOCUMENTS

| | | | | |
|---|---|---|---|---|
| 8,598,309 | B2 * | 12/2013 | Jeong et al. .................... | 528/412 |
| 8,785,592 | B2 * | 7/2014 | Jeong et al. .................... | 528/412 |
| 2003/0045739 | A1 | 3/2003 | Buchanan et al. | |
| 2010/0029896 | A1 * | 2/2010 | Ok et al. ........................ | 528/395 |
| 2010/0121026 | A1 | 5/2010 | Lee et al. | |

FOREIGN PATENT DOCUMENTS

| | | | |
|---|---|---|---|
| KR | 100853358 B1 | 8/2008 | |
| KR | 1020090090154 A | 8/2009 | |
| WO | 2008136591 A1 | 11/2008 | |
| WO | WO 2008136591 * | 11/2008 | ............. C08G 64/20 |

OTHER PUBLICATIONS

Na et al. Inorg. Chem., 2009, 48, 10455-10465.*
Noh et al., "Two Components in a Molecule: Highly Efficient and Thermally Robust Catalytic System for CO2/Epoxide Copolymerization", J. Am. Chem. Soc., 2007, pp. 8082-8083, vol. 129.
Sujith et al., "A Highly Active and Recycable Catalytic System for CO2/Propylene Oxide Copolymerization", Angew. Chem. Int. Ed., 2008, pp. 7306-7309, vol. 47.
Spessard et al., "Organometallic Chemistry", 2000, p. 46, Prentice Hall.
Min et al., "Efficient Synthesis of a Highly Active Catalyst for CO2/Epoxide Copolymerization", Bull. Korean Chem. Soc., Mar. 20, 2009, pp. 745-748, vol. 30, No. 3.
Shan et al., "The Energetics of Hydrogen Bonds in Model Systems: Implications for Enzymatic Catalysis", Science, Apr. 5, 1996, pp. 97-101, vol. 272.
Barnes et al., "(18-Crown-6-K60)potassium 2,4-dinitro-phenolate 2,4-dinitrophenol", Acta Cryst., 2003, pp. m160-m161.
Gilli et al., "Covalent Nature of the Strong Homonuclear Hydrogen Bond. Study of the O—H—O System by Crystal Structure Correlation Methods", J. Am. Chem. Soc., 1994, pp. 909-915, vol. 116.
Magonski et al., "Dissociation Constants of Substituted Phenois and Homoconjugation Constants of the Corresponding Phenol-Phenolate Systems in Acetonitrile", J. Chem. Soc. Faraday Trans., 1993, pp. 119-122, vol. 89, No. 1.
Cohen et al., Cobalt Catalysts for the Alternating Copolymerization of Propylene Oxide and Carbon Dioxide: Combining High Activity and Selectivity, J. Am. Chem. Soc., 2005, pp. 10869-10878, vol. 127.
Na et al., Elucidation of the Structure of a Highly Active Catalytic System for CO2/Epoxide Copolymerization: A salen-Cobaltate Complex of an Unusual Binding Mode, Inorg. Chem., 2009, pp. 10455-10465, vol. 48.
Nakano et al., Selective Formation of Polycarbonate over Cyclic Carbonate: Copolymerization of Epoxides with Carbon Dioxide Catalyzed by a Cobalt(III) Complex with a Piperidinium End-Capping Arm, Angew. Chem. Int. Ed., 2006, pp. 7274-7277, vol. 45.
Qin et al., Cobalt-Based Complexes for the Copolymerization of Propylene Oxide and CO2: Active and Selective Catalysts for Polycarbonate Synthesis, Angew. Chem. Int. Ed., 2003, pp. 5484-5487, vol. 42.
Van Schilt, Carbon Dioxide as a Comonomer for the Production of Aliphatic Polycarbonates: Thermodynamics, Catalysis, and Process Design, Dec. 19, 2006, pp. i-48, Technische Universiteit Eindhoven, Eindhoven, The Netherlands.

* cited by examiner

*Primary Examiner* — Yun Qian
(74) *Attorney, Agent, or Firm* — The Webb Law Firm (57) ABSTRACT

The present invention related to a method of manufacturing a polycarbonate including the process of copolymerizing epoxide compound and CO2 using cobalt(III) or chromium (III), where the ligands contains at least 3 ammonium cations, central metal has formal −1 charge, and conjugated anions of the two cationic ammonium groups are acid-base homoconjugation, as catalyst.
According to the present invention, the initial induction time can be reduced when the said polycarbonate is manufactured and it is possible to improve the activity of the catalyst and the molecular weight of the obtained polymer.

1 Claim, 2 Drawing Sheets

CATALYTIC SYSTEM FOR CO$_2$/EPOXIDE COPOLYMERIZATION

CROSS-REFERENCE TO RELATED APPLICATIONS

This application is a divisional of U.S. patent application Ser. No. 12/817,588, filed on Jun. 17, 2010, which is incorporated herein by reference as if fully set forth and which claims priority to KR 10-2009-0054600 filed on Jun. 18, 2009.

TECHNICAL FIELD

The present invention relates to a method of manufacturing a polycarbonate by copolymerizing epoxides with CO$_2$ using cobalt or chromium complexes, which are prepared from ligand having ammonium salts, as catalyst.

BACKGROUND ART

An aliphatic polycarbonate is a biodegradable copolymer, is a material useful for packages or coatings. The method for preparing a polycarbonate from epoxides and CO$_2$ is highly environmental-friendly considering that any harmful compound phosgene is not used and that CO$_2$ is taken with low cost.

Since 1960s, various types of catalysts have been developed to prepare polycarbonate from epoxides and CO$_2$. Recently, the present inventor has disclosed highly-active and highly-selective catalyst synthesized from Salen[Salen: ([H$_2$Salen=N,N'-bis(3,5-dialkylsalicylidene)-1,2-ethylenediamine]-type ligand including the quaternary ammonium salt [Bun-Yeoul Lee, Korean Patent No. 10-0853358 (Registration date: Aug. 13, 2008); Bun-Yeoul Lee, Sujith S, Eun-Kyung Noh, Jae-Ki Min, Korean Patent Application No. 10-2008-0015454 (Filing date: Feb. 20, 2008); Bun-Yeoul Lee, Sujith S, Eun-Kyung Noh, Jae-Ki Min, PCT/KR2008/002453 (Filing date: Apr. 30, 2008); Eun Kyung Noh, Sung Jae Na, Sujith S, Sang-Wook Kim, and Bun Yeoul Lee*, *J. Am Chem. Soc.* 2007, 129, 8082-8083(2007.07.04); Sujith S, Jae Ki Min, Jong Eon Seong, Sung Jea Na, and Bun Yeoul Lee, *Angew. Chem. Int. Ed.,* 2008, 47, 7306-7309. (2008 Sep. 8)]. The catalyst disclosed by the present inventor shows high-activity and high-selectivity, can be used for preparing high molecular weight copolymer, and is commercially applicable due to the polymerization at high temperature. Furthermore, since the ligand includes the quaternary ammonium salt, it has an advantage of easy recovery and recycling the catalyst after polymerization.

Furthermore, the present inventor has carefully analyzed the structure of the catalyst showing especially high-activity and high-selectivity among a group of catalysts of said patent, and therefore proved that the structure is unique, unknown before in which a nitrogen atom of Salen-ligand is not coordinated but oxygen atoms are coordinated to a metal atom (example 1). Accordingly, the invention relating to a new type of catalyst system obtained from the result filed as Korean Patent Application No. 10-2008-0074435 (Filing: 2008 Jul. 30).

EXAMPLE 1

| | R$^1$ | R$^2$ | R |
|---|---|---|---|
| 1' | H | H | H |
| 2' | —(CH$_2$)$_4$— | | H |
| 3' | —(CH$_2$)$_4$— | | Me |

X = 2,4-dinitrophenolate

The state of dinitrophenolate (DNP) was revealed by the NMR studies of the compound of the example 1. More specifically, two of four DNPs included in the compound are always coordinated to cobalt, and other two of them are fluxional between coordinated state and decoordinated state, where the degree of coordination state can be different according to the change in temperature, solvents, and substituents of ligand (R, R1, R2). The following figure shows the state of DNP according to the catalyst structure at room temperature in THF solvent, which medium is very similar to the polymerization reaction medium. In compound 1', the fluxional motion is too high in time-scale that the signals of the fluxional DNP are not observed in the NMR spectrum. In both complex 2' and 3', the fluxional DNPs stay mostly in a decoordinated state but, those in 2' stay in the decoordinated state for a longer time. That is, the order of the degree of staying in coordinated state of the two fluxional DNPs (i.e. binding affinity to cobalt) is 1'>3'>2'. Whereas, the order of activity (TOF) observed in the CO$_2$/propylene oxide copolymerization is vice versa or 2'>3'>1'. This implies that the activity is lowered if the binding affinity to the cobalt of two fluxional DNPs is high.

The reason why the compound of the above structure shows high activity is explained by the characteristic that two anionic DNP ligands are susceptible for the fluxional movement between the coordinated and decoordinated states. The following figure shows the growth mechanism of the polymer chain for the $CO_2$/epoxide copolymerization. In this mechanism, the attacking of the carbonate anion to the coordinated epoxide is crucial. The fluxional characteristic of the anions enables the carbonate anion to attack the coordinated epoxide from back-side. In chain-growing mechanism shown as below, a high activity is expected if the coordinated carbonate anion can be easily transferred to a decoordinated state.

The [water]/[catalyst] ratio of polymerization solution in the $CO_2$/epoxide copolymerization catalyzed using the said complexes plays an important role in realizing the catalyst activity. Though it is tried to remove water thoroughly from epoxide and $CO_2$, the [water]/[catalyst] ratio is not negligible especially when [epoxide]/[catalyst] ratio is high such as 100,000. At this high [epoxide]/[catalyst] ratio of 100000, the residual small amount water in epoxide and $CO_2$ influences significantly on the [water]/[catalyst] ratio. The high activity (TON) is obtainable only when the polymerization is implemented under the condition of high [epoxide]/[catalyst] ratio such as 100000. Therefore, to be the commercially valuable catalyst, the catalyst should be less sensitive to water. In case of the catalyst having said structure, it was observed that the induction time was highly variable according to the degree of dryness in polymerization solution. For example, when the polymerization reaction is performed in dry winter season, the polymerization reaction shows induction time of about 1-2 hrs, whereas the polymerization shows even 12 hrs when polymerization is performed in humid and hot summer season. Once the polymerization reaction began, activity (TOF) afterwards is not varying. In $^1H$ NMR spectroscopy experiment, it is observed that DNP in the complex attacks propylene oxide. This attacking rate is significantly decreased when water is deliberately added. The two fluxional anions are stabilized through hydrogen bonding with water, thus nucleophilic attacking rate is decreased.

The following table 1 shows the results of terpolymerization reaction with $CO_2$ by mixing propylene oxide (PO) and cyclohexene oxide (CyO) using complex 2' of example 1. As shown in the table 1, it was observed that induction time was varying from 45 min to 9 hr 10 min. Furthermore, it was observed that the molecular weight decreases as induction time increases. This irregular and sometimes long induction time may be an obstacle to the development of commercial process using this catalyst. Additionally, it is inevitably required for commercialization to consistently prepare high molecular weight polymer.

TABLE 1

PO CHO—$CO_2$ terpolymerization results

| PO:CHO | Induction time (min) | Molecular weight (Mn) | Glass transition temperature (Tg, ° C.) | Activity (TOF, h$^{-1}$) |
|---|---|---|---|---|
| 8:2 | 45 | 197000 | 53 | 7200 |
| 7:3 | 105 | 180000 | 60 | 6700 |
| 6:4 | 160 | 148000 | 63 | 7600 |
| 5:5 | 40 | 149000 | 70 | 7000 |

TABLE 1-continued

PO CHO—$CO_2$ terpolymerization results

| PO:CHO | Induction time (min) | Molecular weight (Mn) | Glass transition temperature (Tg, ° C.) | Activity (TOF, h$^{-1}$) |
|---|---|---|---|---|
| 4:6 | 400 | 66000 | 73 | 11000 |
| 3:7 | 450 | 68000 | 87 | 8500 |
| 2:8 | 550 | 57000 | 95 | 7000 |

DISCLOSURE

Technical Problem

An object of the present invention is to solve the problems that induction time of the above catalyst system is irregular and long, that low molecular weight polymer is obtained, and that the activity of the catalyst lowers, in the manufacturing a polycarbonate by copolymerizing $CO_2$ with epoxide.

Technical Solution

To achieve the above object, the present invention provides a method of manufacturing a polycarbonate including the step of copolymerizing epoxide compound and $CO_2$ using cobalt(III) or chrome(III) complexes(formula 1), where the ligands contains at least 3 ammonium cations, central metal has formal −1 charge, and conjugated anions of the two cationic ammonium groups are acid-base homoconjugation, as catalyst.

$$[L^1L^2L^3L^4M]^-[X^1\ldots H\ldots X^2]^-_a Z^-_b \qquad \text{[Formula 1]}$$

where, M is cobalt(III) or chrome(III);

$L^1$ to $L^4$ are anionic X-type ligands, $L^1$ to $L^4$ are same or different respectively, also is able to form bidentate, tridentate or tetradentate by linking each other, at least one of $L^1$ to $L^4$ include quaternary ammonium salt, the number of total ammonium cation included in $L^1$ to $L^4$ is 1+a+b, and hence the complex is overall neutral;

a or b is an integer; preferably a or b is a integer of 0 to 15 but not limited thereto, and that is satisfied in 1+a+b.

The ligand(s) among $L^1$ to $L^4$ except the ligand including the quaternary ammonium cation, or $X^1$ and $X^2$ are each other independently halogen anion or $HCO_3^-$, or aryloxy anion having carbon number 6 to 20 including or non-including one or more of halogen atom, nitrogen atom, oxygen atom, silicon atom, sulfur atom and phosphor atom, carboxy anion having carbon number 1 to 20; alkoxy anion having carbon number 1 to 20; carbonate anion having carbon number 1 to 20; alkylsulfonate anion having carbon number 1 to 20; amide anion having carbon number 1 to 20; carboxamide anion having carbon number 1 to 20; sulfonamide anion having carbon number 1 to 20; or carbamate anion having carbon number 1 to 20, Z is $BF_4^-$, $ClO_4^-$, $NO_3^-$ or $PF_6^-$.

The X-type ligand is described in detail in Gary O, Spessard and Gary L. Miessler, *Organometallic Chemistry*, p. 46, Prentice Hall. The X-type ligand is anionic ligand such as hydrogen, chlorine or methyl, $X^-$ anion is considered to conjugate to a metal element M+ cation, and the binding of X-type ligand affects oxidation state of metal.

The embodiment of the present invention provides a method for manufacturing a polycarbonate including a step of copolymerizing epoxide compound with $CO_2$ using the catalyst represented by the following formula 2.

[Formula 2]

where, $L^5$, $L^6$, $X^3$ or $X^4$ is each other independently, halogen anion or $HCO_3^-$, or aryloxy anion having carbon number 6 to 20 including or non-including one or more of halogen atom, nitrogen atom, oxygen atom, silicon atom, sulfur atom and phosphor atom, carboxy anion having carbon number 1 to 20; alkoxy anion having carbon number 1 to 20; carbonate anion having carbon number 1 to 20; alkylsulfonate anion having carbon number 1 to 20; amide anion having carbon number 1 to 20; carboxamide anion having carbon number 1 to 20; sulfonamide anion having carbon number 1 to 20; or carbamate anion having carbon number 1 to 20, c is 1 or 0, Z is $BF_4^-$, $ClO_4^-$, $NO_3^-$ or $PF_6^-$,

$R^{12}$ and $R^{14}$ may selected from methyl, ethyl, isopropyl or hydrogen, $R^{11}$ and $R^{13}$ is $-[CH\{(CH_2)_3N+Bu_3\}_2]$ or $-[CMe\{(CH_2)_3N+Bu_3\}_2]$, Q is diradical which binds in order to connect two nitrogen atoms, said Q is (C6~C30)arylene, (C1~C20)alkylene, (C2~C20)alkenylene, (C2~C20)alkynylene, (C3~C20)cycloalkylene or a combined (C3~C20)cycloalkylene, or said arylene, alkylene, alkenylene, alkynylene, cycloalkylene or a combined cycloalkylene can be substituted with a substituent group selected from a halogen atom, (C1~C7)alkyl, (C6~C30)aryl or nitro group, or include one or more hetero atom selected from oxygen, sulfur and nitrogen.

More specifically, in the formula 2, Q is trans-1,2-cyclohexylene or ethylene; X is 2,4-dinitrophenolate, 4-nitrophenolate, 2,4,5-trichlorophenolate, 2,4,6-trichlorophenolate, or pentafluorophenolate; Z is $BF_4^-$.

More preferably, the present invention provides a method of manufacturing a polycarbonate including a step of copolymerizing epoxide with $CO_2$ using a catalyst of the following formula 3.

[Formula 3]

where, $L^7$, $L^8$, $X^5$ or $X^6$ is separately independently, halogen anion or $HCO_3^-$, or aryloxy anion having carbon number 6 to 20 including or non-including one or more of halogen atom, nitrogen atom, oxygen atom, silicon atom, sulfur atom and phosphor atom, carboxy anion having carbon number 1 to 20; alkoxy anion having carbon number 1 to 20; carbonate anion having carbon number 1 to 20; alkylsulfonate anion having carbon number 1 to 20; amide anion having carbon number 1 to 20; carboxamide anion having carbon number 1 to 20; sulfonamide anion having carbon number 1 to 20; or carbamate anion having carbon number 1 to 20, Z is $BF_4^-$, $ClO_4^-$, $NO_3^-$ or $PF_6^-$, $R^{12}$ and $R^{14}$ may selected from methyl, ethyl, isopropyl or hydrogen, $R^{11}$ and $R^{13}$ is $-[CH\{(CH_2)_3N+Bu_3\}_2]$ or $-[CMe\{(CH_2)_3N+Bu_3\}_2]$, Q is diradical which binds in order to two nitrogen atoms, said Q is (C6~C30)arylene, (C1~C20)alkylene, (C2~C20) alkenylene, (C2~C20)alkynylene, (C3~C20)cycloalkylene or a combined (C3~C20)cycloalkylene, or said arylene, alkylene, alkenylene, alkynylene, cycloalkylene or a combined cycloalkylene can be substituted with a substituent group selected from a halogen atom, (C1~C7)alkyl, (C6~C30)aryl or nitro group, or include one or more hetero atom selected from oxygen, sulfur and nitrogen.

More specifically, in the formula 3, Q is trans-1,2-cyclohexylene or ethylene; X is 2,4-dinitrophenolate, 4-nitrophenolate, 2,4,5-trichlorophenolate, 2,4,6-trichlorophenolate, or pentafluorophenolate; Z is $BF_4^-$.

The complex according to the present invention is manufactured by the method of manufacturing a catalyst, including synthesizing ligand having ammonium salts, reacting a metal acetate (where metal is cobalt or chromium) with the ligand having ammonium salt, removing the generated acetic acid to obtain cobalt(II) complexes, and oxidizing them using oxygen as oxidizing agent in the presence of adequate acid (HX) to obtain cobalt(III) compound, and then anion exchange reaction using 60~100 mol % of NaX. The ligand having ammonium salt is manufactured according to the present inventors published method (*Bull. Korean Chem. Soc.* 2009, 30, 745).

X in the acid (HX) is halogen anion or $HCO_3^-$, or aryloxy anion having carbon number 6 to 20 including or non-including one or more of halogen atom, nitrogen atom, oxygen atom, silicon atom, sulfur atom and phosphor atom, carboxy anion having carbon number 1 to 20; alkoxy anion having carbon number 1 to 20; carbonate anion having carbon number 1 to 20; alkylsulfonate anion having carbon number 1 to 20; amide anion having carbon number 1 to 20; carboxamide anion having carbon number 1 to 20; sulfonamide anion having carbon number 1 to 20; or carbamate anion having carbon number 1 to 20.

The present invention provides a method of manufacturing a polycarbonate including a step of polymerizing epoxide compound and $CO_2$ using cobalt complex selected from the said formula 1 to 3 as catalyst.

The said epoxide compound can be selected from the group consisting of (C2~C20)alkyleneoxide substituted or unsubstituted with halogen or alkoxy; (C4~C20)cycloalkyleneoxide substituted or unsubstituted with halogen or alkoxy; and (C8~C20)styreneoxide substituted or unsubstituted with halogen, alkoxy, alkyl or aryl. The said alkoxy is specifically alkyloxy, aryloxy, aralkyloxy, etc., the said aryloxy is phenoxy, biphenyloxy, naphtyloxy, etc. The said alkoxy, alkyl and aryl can be one having substituents selected from halogen atom or alkoxy group.

The said epoxide compound is, for example, ethylene oxide, propylene oxide, butene oxide, pentene oxide, hexene oxide, octene oxide, decene oxide, dodecene oxide, tetradecene oxide, hexadecane oxide, octadecene oxide, butadiene monoxide, 1,2-epoxide-7-octene, epifluorohydrine, epichlorohydrine, epibromohydrine, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxidnobonene, limonene oxide, dieldrine, 2,3-epoxidepropylbenzene, styrene oxide, phenylpropylene oxide, stylbene oxide, chlorostylbene oxide, dichlorostylbene oxide, 1,2-epoxy-3-phenoxypropane, benzyloxymethyl oxirane, glycidyl-methylphenyl ether, chlorophenyl-2,3-epoxidepropyl ether, epoxypropyl methoxyphenyl ether, biphenyl glycidyl ether, glycidyl naphtyl ether, etc.

The epoxide compound can be used for polymerization using organic solvent as reaction medium, and the said solvent is, for example, an aliphatic hydrocarbon such as pentane, octane, decane and cyclohexane, etc., an aromatic hydrocarbon such as benzene, toluene, and xylene, etc., and halogenated hydrocarbon such as chloromethane, methylenechloride, chloroform, carbontetrachloride, 1,1-dichloroethane, 1,2-dichloroethane, ethylchloride, trichloroethane, 1-chloropropane, 2-chloropropane, 1-chlorobutane, 2-chlorobutane, 1-chloro-2-methylpropane, chlorobenzene and bromobenzene, etc., it can be used single or combination of two or more. More preferably, bulk polymerization using monomer itself as solvent can be performed.

Molar ratio of an epoxide compound to a catalyst, that is, an epoxide compound: a catalyst is useful at 1,000 to 1,000,000, preferably 50,000 to 200,000.

In the said copolymerization step, the pressure of $CO_2$ is atmospheric pressure to 100 bar, preferably 5 bar to 30 bar.

The polymerization temperature in the copolymerization is 20° C. to 120° C., preferably 50° C. to 90° C.

As the method of polymerizing polycarbonate, it can be used batch polymerization, semibatch polymerization, or continuous polymerization. In case of batch polymerization or semibatch polymerization, the reaction time is 1 to 24 hrs, preferably 1.5 to 4 hrs. The average retention time of the catalyst in continuous polymerization is also preferably 1.5 to 4 hrs.

According to the present invention, the polycarbonate that number-average molecular weight (Mn) is 5,000 to 1,000,000 and molecular weight distribution (that is, Mw/Mn) is 1.05 to 4.0, can be manufactured. In the above, Mn means number-average molecular weight measured on GPC using polystyrene standards. The molecular weight distribution value (Mw/Mn) is the ratio between weight-average molecular weight (Mw) and number-average molecular weight (Mn) measured on GPC.

The obtained polycarbonate polymer comprises 80% or more carbonate linkages, frequently 95% or more carbonate linkages. The polycarbonate manufactured according to the present invention is easily degradable, has no residue and soot in combustion, and is a useful material as for example, packages, insulator or coatings.

Advantageous Effects

As described above, the reason why the conventional catalyst shows high activity is due to the fluxional characteristic of two anionic ligands between coordinated and decoordinated states. Further, if the fluxional anionic ligands could easily decoordinated from metal center, that is, when less interacts with metal center, the activity increases. The present invention relates to increasing the activity by weakening the interaction of anion with metal center, by substituting the fluxional anionic ligand with acid-base homoconjugation, for example [DNP . . . H . . . DNP]⁻ (refer to table 2 and table 3). If the activity of the catalyst increases, generally the molecular weight increases (refer to table 2 and table 3). Further, the sensitivity to the water can be reduced by substituting two anions with acid-base homoconjugation (refer to table 2 and table 3). As described above, in the case of the existing catalyst, the induction time varies largely according to the level of dryness in polymerization solution; it was explained as the fluxional anion forms hydrogen-bonds with water which reduces the nucleophilic attack of the anion onto propylene oxide. In the case of acid-base homoconjugation, hydrogen bonds exist already in it and the sensitivity to water is relaxed, consequently the variation of induction time being relatively less.

Figure 1:
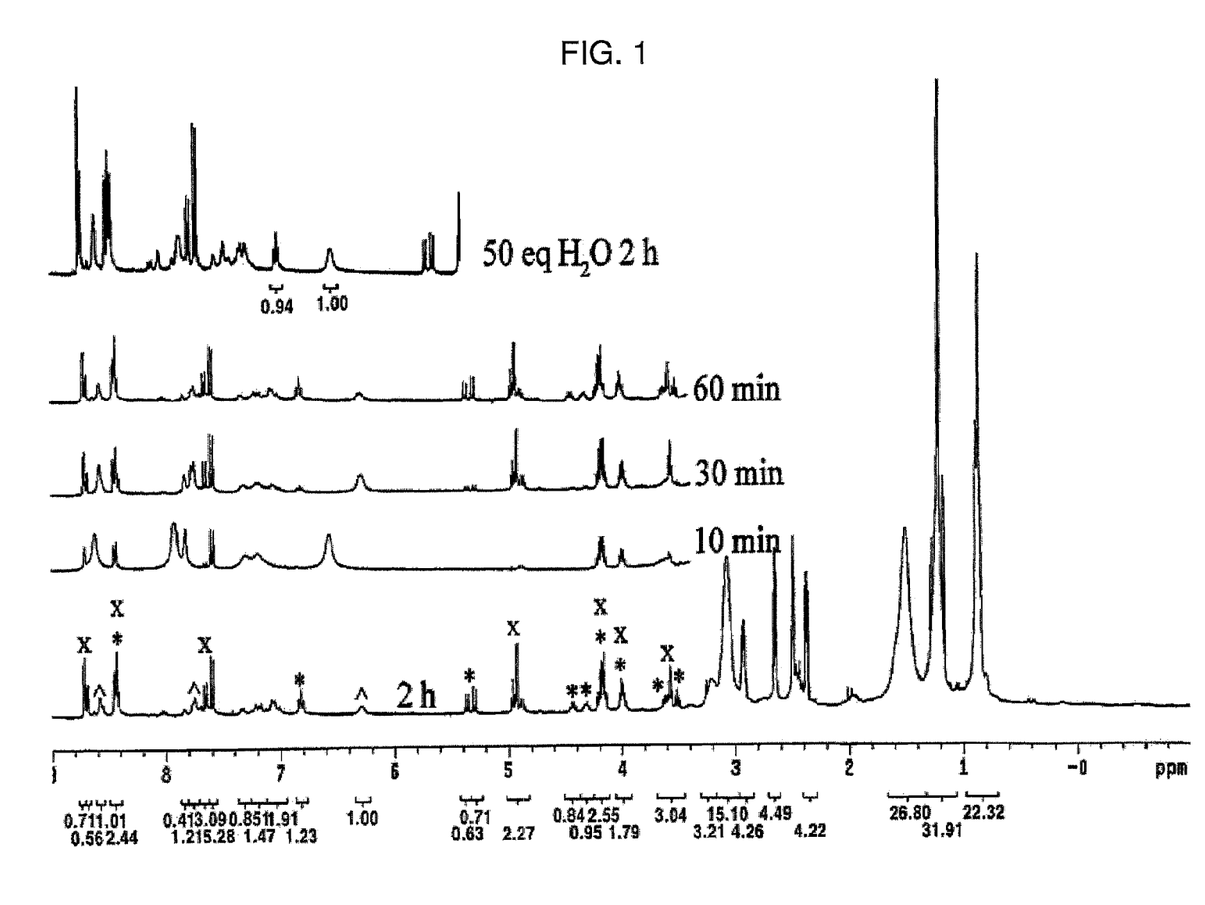
FIG. 1 is $^1$H NMR spectrum in dmso-d$_6$ showing the reaction between compound 4 and propylene oxide. The signal marked with * is anion of Meisenheimer salt which produced by DNP anion's reaction, the signal marked with x is 2,4-(NO$_2$)$_2$C$_6$H$_3$—OCH$_2$CH(Me)OH and 2,4-(NO$_2$)$_2$C$_6$H$_3$—OCH(Me)CH$_2$OH, the signal marked with ˆ is DNP.
Figure 2:
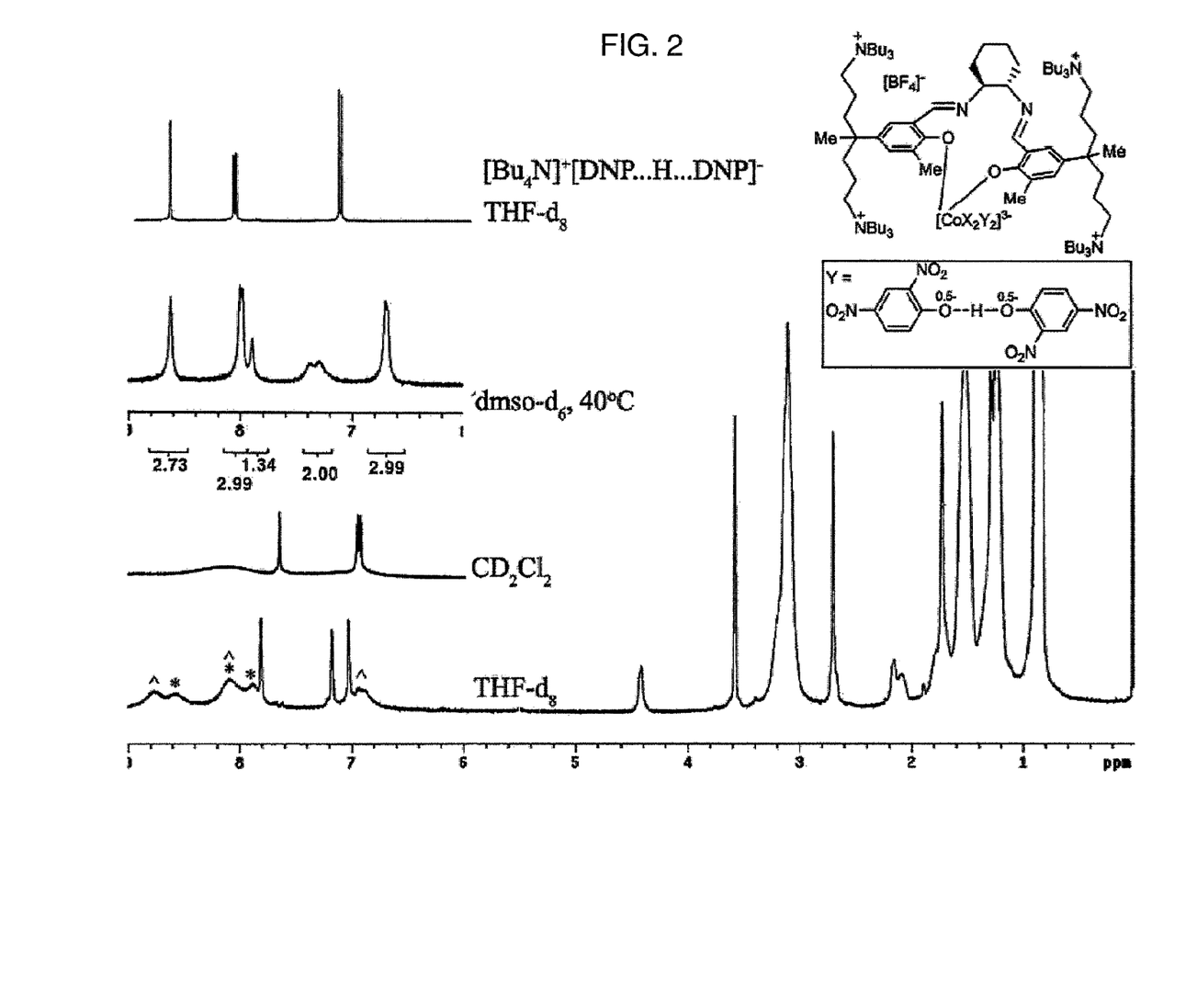
FIG. 2 is $^1$H NMR spectrum of compound 4 that measured in thf-d8 solvent. The signal marked with * is a coordinated DNP signal, the signal marked with ˆ is a homoconjugation signal.

If DNP forms hydrogen bonding with water, its nucleophilicity is lowered, thereby the reaction rate with PO is lowered, however, in the case of the homoconjugation, it forms hydrogen-bonding in itself, but the nucleophilic attacking rate to PO improves on the contrary. FIG. 1 is $^1$H NMR spectrum, showing the reaction between compound 6 of the following formula 4 and propylene oxide. It could be observed that the homoconjugation reacts with propylene oxide, the anion of Meisenheimer salt (the signal marked with *) and alcohol compound 2,4-$(NO_2)_2C_6H_3$—$OCH_2CH(Me)OH$ and 2,4-$(NO_2)_2C_6H_3$—$OCH(Me)CH_2OH$ (the signal marked with x) was formed, the coordinated DNP (the signal marked with ˆ) is exist as it is. When the activity of the compound 3 and 6 and with propylene oxide is counted by numbering the reacted propylene oxide for early 30 minutes, it could be seen the compound 6 is twice as fast as, and these results are same as the results that the activity of compound 6 is higher than that of compound 3. Also, in case of compound 4, the activity with propylene oxide is largely lowered by adding 50 equivalent of water, however as seen in FIG. 1, the activity of the compound 6 with propylene oxide in the presence of 50 equivalent of water is not lowered. This result explains the reason why the sensitivity of compound 6 to water is less than that of the compound 3.

[Formula 4]

|   | Y | d |
|---|---|---|
| 4 | 2,4-dinitrophenolate | 1 |
| 5 | 4-nitrophenolate | 1 |
| 6 | 2,4,5-trichlorophenolate | 0 |
| 7 | 2,4,6-trichlorophenolate | 0 |
| 8 | pentafluorophenolate | 1 |

[Formula 5]

|   | W | e |
|---|---|---|
| 3 | 2,4-dinitrophenolate | 1 |
| 9 | 4-notrophenolate | 1 |
| 10 | 2,4,5-trichlorophenolate | 0 |
| 11 | 2,4,6-trichlorophenolate | 0 |
| 12 | pentafluorophenolate | 1 |

$[Y...H...Y]_{(3-d)}^- [BF_4]_d^-$ $[W]_{(3-e)}^- [BF_4]_e^-$

[Reaction formula 1]

K = 2, 4-dinitrophenolate

The strength of hydrogen bonds in acid-base homoconjugation is much higher than the general strength of hydrogen bonds. In the reference in Shan, S.-o. and Loh, S, and Herschlag, D, *Science* 1996, 272, 97, it is reported that in the case of forming hydrogen bonds between the acid and base of which $PK_a$ value is same, the strength of hydrogen bonds is unusually bigger, thereby the activity of enzyme is maximized. Further, in the x-ray single crystal structure of (18-Crown-6-k$^6$O) potassium 2,4-dinitrophenolate 2,4-dinitrophenol homoconjugation that is reported by Barnes, J. C. and Weakley, T. J. R., *Acta Cryst.* 2003, E59, m160, the length of oxygen-oxygen bonds connected by hydrogen bonds is 2.453(4)Å. This bond length supports the very strong hydrogen bonds. (Paola Gilli, P.; Bertolasi, V.; Ferretti, V.; and Gilli, V. *J. Am. Chem. Sec.* 1994, 116, 909.). Also, in the reference Magonski, J. and Pawlak, Z and Jasinski, T, *J. Chem. Soc. Faraday Trans.* 1993, 89, 119, the equilibrium constant to homoconjugation forming is about 100, and two components in organic solvent exist as homoconjugation as suggested by formula 4. In practice, in the $^1$H NMR spectrum of compound 6 that are measured in thf-d$_8$ solvent, the coordinated DNP signal marked with * and the homoconjugation [DNP . . . H . . . DNP]$^-$ signal marked with could be seen clearly.

BEST MODE

Hereinafter, the present invention will be described in more detail with reference to the following Examples, but the scope of the present invention is not limited thereto.

PREPARING EXAMPLE 1

Synthesis of 60 mol % sodium dinitrophenolate(NaDNP)

A commercially available dinitrophenol (10.0 g, 54.3 mmol) was dissolved in 250 mL of methylenechloride, and water was removed on anhydrous magnesium sulfate. Solvent was removed by filtration under the reduced pressure. After the anhydrous dinitrophenol (10.0 g, 54.3 mmol) was dissolved in anhydrous THF (300 mL), NaH(0.782 g, 32.6 mmol) was added slowly. After all NaH was added, the solution was stirred for 3 hrs. Solvent was removed under reduced pressure to obtain 60 mol % sodium dinitrophenolate.

PREPARING EXAMPLE 2

Synthesis of 100 mol % sodium dinitrophenolate

The anhydrous dinitrophenol (10.0 g, 54.3 mmol) was dissolved in anhydrous THF (300 mL) and then NaH(1.30 g, 54.3 mmol) was added slowly. After the solution was stirred for 3 hrs, solvent was removed under the reduced pressure to obtain 100 mol % sodium dinitrophenolate.

EXAMPLE

[Formula 4]

| | Y | d |
|---|---|---|
| 4 | 2,4-dinitrophenolate | 1 |
| 5 | 4-nitrophenolate | 1 |
| 6 | 2,4,5-trichlorophenolate | 0 |
| 7 | 2,4,6-trichlorophenolate | 0 |
| 8 | pentafluorophenolate | 1 |

[Y . . . H . . . Y]$_{(3-d)}^-$ [BF$_4$]$_d^-$

Example 1

Synthesis of Compound 4

The ligand was synthesized according to the published reference (*Bull. Korean Chem. Soc.* 2009, 30, 745). In the glove box, after ligand (0.376 g, 0.230 mmol) and Co(OAc)$_2$ (0.041 g, 0.230 mmol) was quantitatively added in 50 mL round flask, ethanol (17 mL) was added and the resulting solution was stirred for 3 hrs. Diethyl ether (20 mL) was added to precipitate a solid which was filtered using a glass filter, and then washed with diethyl ether (10 mL) three times. The solvent in the obtained orange solid was completely removed under the reduced pressure. 2,4-Dinitrophenol (0.022 g, 0.117 mmol) was added to a flask containing the above prepared Co(II) compound(0.200 g, 0.117 mmol), and the methylene chloride (5 mL) was added. After the solution was stirred for 3 hrs under oxygen atmosphere, the above prepared 60 mol % sodium dinitrophenolate (0.121 g, 0.585 mmol) was added and agitated for 12 hrs. After the solution was filtered using a glass filter, solvent was removed under the reduced pressure to obtain a reddish brown solid (0.284 g, 0.111 mmol). Yields 95%. $^1$H NMR (dmso-d$_6$, 40° C.): δ 8.62 (br, 3H, (NO$_2$)$_2$C$_6$H$_3$O), 8.03 (br, 3H, (NO$_2$)$_2$C$_6$H$_3$O), 7.87 (br, 1H, CH=N), 7.41-7.22 (br, 2H, m-H), 6.71 (br, 3H, (NO$_2$)$_2$C$_6$H$_3$O), 3.62 (br, 1H, cyclohexyl-CH), 3.08 (br, 16H, NCH$_2$), 2.62 (s, 3H, CH$_3$), 2.09 (1H, cyclohexyl-CH), 1.89 (1H, cyclohexyl-CH), 1.72-1.09 (br, 37H), 0.87 (br, 18H, CH$_3$) ppm.

Example 2

Synthesis of Compound 5

The compound 5 was synthesized by the same method as compound 4 using 4-nitrophenol. The reaction rate of $O_2$-oxidation was slow, so the reaction was performed for 3 days. The anion exchange reaction was performed using 60 mol % sodium 4-nitrophenolate which are manufactured according to the method of manufacturing above 60 mol % sodium 2,4-dinitrophenolate. Yields 95%. $^1$H NMR (dmso-$d_6$, 40° C.): δ 7.96 (br, 4H, $(NO_2)C_6H_4O$), 7.77 (br, 1H, CH=N), 7.49 (br, 1H, $(NO_2)C_6H_4O$) 7.10 (br, 1H, m-H), 7.02 (br, 2H, m-H, $(NO_2)C_6H_4O$), 6.56 (br, 4H, $(NO_2)C_6H_4O$), 3.97 (br, 1H, cyclohexyl-CH), 2.96 (br, 16H, $NCH_2$), 2.61 (s, 3H, $CH_3$), 2.09 (1H, cyclohexyl-CH), 1.89 (1H, cyclohexyl-CH), 1.55-1.05 (br, 37H), 0.87 (br, 18H, $CH_3$) ppm.

Example 3

Synthesis of Compound 6

The compound was synthesized by the same method as compound 4 using 2,4,5-trichlorophenol. The reaction rate of $O_2$-oxidation was slow, so the reaction was performed for 3 days. The anion exchange reaction was performed using 60 mol % sodium 2,4,5-trichlorophenolate which are manufactured according to the method of manufacturing above 60 mol % sodium 2,4,5-trichlorophenolate. Yields 95%. $^1$H NMR (dmso-$d_6$, 40° C.): δ 8.34 (s, 1H, $C_6H_2Cl_3O$), 7.70 (s, 1H, CH=N), 7.39 (s, 2H, $C_6H_2Cl_3O$), 7.09 (s, 1H, m-H), 6.97 (s, 1H, m-H), 6.85 (s, 2H, $C_6H_2Cl_3O$), 6.69 (s, 1H, $C_6H_2Cl_3O$), 4.13 (br, 1H, cyclohexyl-CH), 2.99 (br, 16H, $NCH_2$), 2.63 (s, 3H, $CH_3$), 2.10 (br, 1H, cyclohexyl-$CH_2$), 1.84 (br, 1H, cyclohexyl-$CH_2$), 1.57-1.05 (br, 37H), 0.84 (br, 18H, $CH_3$) ppm.

Example 4

Synthesis of Compound 7

The compound 7 was synthesized by the same method as compound 4 using 2,4,6-trichlorophenol. The reaction rate of $O_2$-oxidation was slow, so the reaction was performed for 3 days. The anion exchange reaction was performed using 60 mol % sodium 2,4,6-trichlorophenolate which are manufactured according to the method of manufacturing above 60 mol % sodium 2,4,6-trichlorophenolate. Yields 98%. $^1$H NMR (dmso-$d_6$, 40° C.): δ 7.92 (br, 1H, CH=N), 7.44 (br, 1H, m-H), 7.31 (br, 1H, m-H), 7.20 (br, 6H, $C_6H_3Cl_3O$), 3.60 (br, 1H, cyclohexyl-CH), 3.10 (br, 16H, $NCH_2$), 2.65 (s, 3H, $CH_3$), 2.01 (br, 1H, cyclohexyl-$CH_2$), 1.83 (br, 1H, cyclohexyl-$CH_2$), 1.66-1.15 (br, 37H), 0.88 (br, 18H, $CH_3$) ppm.

Example 5

Synthesis of Compound 8

The compound 8 was synthesized by the same method as compound 4 using pentafluorophenol. The reaction rate of $O_2$-oxidation was slow, so the reaction was performed for 3 days. The anion exchange reaction was performed using 60 mol % sodium pentafluorophenol which are manufactured according to the method of manufacturing above 60 mol % sodium pentafluorophenol. Yields 97%. $^1$H NMR (dmso-$d_6$, 40° C.): δ 7.85 (br, 1H, CH=N), 7.18 (br, 1H, m-H), 7.10 (br, 1H, m-H), 4.03 (br, 1H, cyclohexyl-CH), 3.09 (br, 16H, $NCH_2$), 2.46 (br, 3H, $CH_3$), 2.09 (br, 1H, cyclohexyl-$CH_2$), 1.87 (br, 1H, cyclohexyl-$CH_2$), 1.70-1.15 (br, 37H), 0.88 (br, 18H, $CH_3$) ppm.

Example 6-10

$CO_2$/propylene oxide copolymerization

After the compound 4-8 that was manufactured in above example 1-5(0.0027 mmol, monomer/catalyst=50,000) and propyleneoxide (7.71 g, 135 mmol) were added 50 mL bomb reactor, the reactor was assembled. The reactor was immersed in the oil bath of which temperature was controlled to 80° C., and then was stirred for about 15 minutes to make the solution temperature reach the bath temperature. The $CO_2$ gas was charged at 20 bar pressure. It could be observed that the $CO_2$ pressure was dropped by the progress of the polymerization. The reaction was terminated by removing $CO_2$ gas at pressure drop of 7 bar (30 min reaction). The 10 g of monomer was further added in the obtained viscous solution to reduce the viscosity, and then the solution was passed through the silica gel (400 mg, Merck, 0.040-0.063 mm size (230-400 mesh)) pad to obtain colorless solution. The white solid of polymer was obtained by removing the monomer under the reduced pressure. TON (Turnover Number) and TOF (Turnover Frequency) were calculated by measuring the weight, the molecular weight of above obtained polymer was measured using GPC. The selectivity to polymer formation versus propylene carbonate was calculated by analyzing the $^1$H NMR spectrum. The following table 2 shows the polymerization results.

TABLE 2

The polymerization result of $CO_2$/propylene oxide of Example 6-10

| Example | Catalyst | Induction time (min) | TOF (h−1) | Selectivity (%) | Molecular weight (Mn) ×10$^{-3}$ | Molecular weight distribution (Mw/Mn) |
|---|---|---|---|---|---|---|
| 6[a] | 4 | 60 | 15000 | 99 | 270 | 1.26 |
| 7 | 5 | 0 | 13000 | 95 | 240 | 1.36 |
| 8 | 6 | 0 | 16000 | 94 | 190 | 1.43 |
| 9 | 7 | 60 | 7400 | 85 | 90 | 1.32 |
| 10 | 8 | 60 | 12000 | 94 | 170 | 1.35 |

[a]monomer/catalyst = 100,000

Comparative Example

[Formula 5]

| W | | e |
|---|---|---|
| 3 | 2,4-dinitrophenolate | 1 |
| 9 | 4-notrophenolate | 1 |
| 10 | 2,4,5-trichlorophenolate | 0 |
| 11 | 2,4,6-trichlorophenolate | 0 |
| 12 | pentafluorophenolate | 1 |

$[W]_{(3-e)}^- [BF_4]_e^-$

Comparative Example 1

Synthesis of Compound 3

After Co (III) compound was formed by the method as the manufacturing method of compound 4, the anion exchange reaction was performed by using the above obtained 100 mol % sodium dinitrophenolate (5 equivalent). Yields 94%. $^1$H NMR (dmso-$d_6$, 40° C.): δ 8.59 (br, 2H, $(NO_2)_2C_6H_3O$), 7.89 (br, 1H, CH=N), 7.79 (br, 2H, $(NO_2)_2C_6H_3O$), 7.41-7.18 (br, 2H, m-H), 6.32 (br, 2H, $(NO_2)_2C_6H_3O$), 3.62 (br, 1H, cyclohexyl-CH), 3.08 (br, 16H, NCH$_2$), 2.62 (s, 3H, CH$_3$), 2.08 (1H, cyclohexyl-CH), 1.82 (1H, cyclohexyl-CH), 1.69-1.05 (br, 37H), 0.83 (br, 18H, CH$_3$) ppm.

Comparative Example 2

Synthesis of Compound 9

After Co (III) compound was formed by the method as the manufacturing method of compound 5, the anion exchange reaction was performed by using the above obtained 100 mol % sodium 4-nitrophenolate (5 equivalent). Yield 98%. $^1$H NMR (dmso-$d_6$, 40° C.): δ 7.75 (br, 2H, $C_6H_4NO_2O$), 7.66 (br, 1H, CH=N), 7.37 (br, 2H, $C_6H_4NO_2O$), 6.98 (br, 1H, m-H), 6.91 (br, 3H, m-H, $C_6H_4NO_2O$), 6.21 (br, 2H, $C_6H_4NO_2O$), 3.85 (br, 1H, cyclohexyl-CH), 2.86 (br, 16H, NCH$_2$), 2.50 (s, 3H, CH$_3$), 1.98 (br, 1H, cyclohexyl-CH$_2$), 1.78 (br, 1H, cyclohexyl-CH$_2$), 1.56-0.90 (br, 37H), 0.72 (br, 18H, CH$_3$) ppm.

Comparative Example 3

Synthesis of Compound 10

After Co (III) compound was formed by the method as the manufacturing method of compound 6, the anion exchange reaction was performed by using the above obtained 100 mol % sodium 2,4,5-trichlorophenolate (5 equivalent). Yield, 94%. $^1$H NMR (dmso-$d_6$, 40° C.): δ 8.34 (s, 1H, $C_6H_2Cl_3O$), 7.70 (s, 1H, CH=N), 7.11 (s, 1.5H, $C_6H_2Cl_3O$), 7.09 (s, 1H, m-H), 6.97 (s, 1H, m-H), 6.69 (s, 1H, $C_6H_2Cl_3O$), 6.39 (s, 1.5H, $C_6H_2Cl_3O$), 4.13 (br, 1H, cyclohexyl-CH$_2$), 1.84 (br, 1H, cyclohexyl-CH$_2$), 1.57-1.05 (br, 37H), 0.84 (br, 18H, CH$_3$) ppm.

Comparative Example 4

Synthesis of Compound 11

After Co (III) compound was formed by the method as the manufacturing method of compound 6, the anion exchange reaction was performed by using the above obtained 100 mol % sodium 2,4,6-trichlorophenolate (5 equivalent). Yield, 99%. $^1$H NMR (dmso-$d_6$, 40° C.): δ 7.99 (br, 1H, CH=N), 7.46 (br, 1H, m-H), 7.31 (br, 1H, m-H), 6.91 (br, 5H, $C_6H_2Cl_3O$), 3.55 (br, 1H, cyclohexyl-CH$_2$), 3.08 (br, 16H, NCH$_2$), 2.62 (s, 3H, CH$_3$), 2.00 (br, 1H, cyclohexyl-CHA, 1.80 (br, 1H, cyclohexyl-CHA, 1.70-1.15 (br, 37H), 0.87 (br, 18H, CH$_3$) ppm.

Comparative Example 5

Synthesis of Compound 12

After Co(III) compound was formed by the method as the manufacturing method of compound 6, the anion exchange reaction was performed by using the above obtained 100 mol % sodium pentafluorophenolate (5 equivalent). Yield, 97%. $^1$H NMR (dmso-$d_6$, 40° C.): δ 7.85 (br, 1H, CH=N), 7.18 (br, 1H, m-H), 7.10 (br, 1H, m-H), 4.03 (br, 1H, cyclohexyl-CH), 3.09 (br, 16H, NCH$_2$), 2.46 (br, 3H, CH$_3$), 2.07 (br, 1H, cyclohexyl-CH$_2$), 1.89 (br, 1H, cyclohexyl-CHA, 1.70-1.15 (br, 37H), 0.88 (br, 18H, CH$_3$) ppm.

Comparative Example 6-10

CO$_2$/propylene oxide copolymerization

The polymerizations were performed by using the catalyst of formula 5. The following table 3 shows the polymerization results.

TABLE 3

CO$_2$/propylene oxide copolymerization results of comparative example 6-10

| Example | Catalyst | Induction time (min) | TOF ($h^{-1}$) | Selectivity (%) | Molecular weight (Mn) × $10^{-3}$ | Molecular weight distribution (Mw/Mn) |
|---|---|---|---|---|---|---|
| 6[a] | 3 | 240[b] | 10000 | 99 | 140 | 1.17 |
| 7 | 9 | 0 | 7900 | 93 | 170 | 1.31 |
| 8 | 10 | 0 | 10000 | 94 | 170 | 1.37 |
| 9 | 11 | 0 | 0 | | | |
| 10 | 12 | 240 | 8400 | 94 | 140 | 1.30 |

[a]monomer/catalyst = 100,000;
[b]the induction time is not consistent, the value of 60~600 minutes was observed.

The invention claimed is:
1. A method of manufacturing polycarbonate comprising the step of:
copolymerizing an epoxide compound and CO$_2$ with a complex having the structure of the following formula 4 as a catalyst, in which the epoxide compound is optimally selected from the group consisting of (C2~C20) alkyleneoxide substituted or unsubstituted with halogen or alkoxy; (C4~C20)cycloalkyleneoxide substituted or unsubstituted with halogen or alkoxy; and (C8~C20) styreneoxide substituted or unsubstituted with halogen, alkoxy, alkyl or aryl:

[formula 4]

| Y | | d |
|---|---|---|
| 4 | 2,4-dinitrophenolate | 1 |
| 5 | 4-nitrophenolate | 1 |
| 6 | 2,4,5-trichlorophenolate | 0 |
| 7 | 2,4,6-trichlorophenolate | 0 |
| 8 | pentafluorophenolate | 1 |

$[Y\ldots H\ldots Y]_{(3-d)}^{-} [BF_4]_d^{-}$ wherein H is hydrogen in $[Y\ldots H\ldots Y]^{-}$ as acid-base homoconjugation, and H is hydrogen bonded between Y and Y.

\* \* \* \* \*